United States Patent
Pauly (10) Patent No.: US 6,184,199 B1
(45) Date of Patent: Feb. 6, 2001

(54) ACTIVE SYNERGETIC COMPLEX AND COSMETIC AND/OR PHARMACEUTICAL PRODUCT CONTAINING THIS COMPLEX

(75) Inventor: Gilles Pauly, Nancy (FR)

(73) Assignee: Laboratoires Serobiologiques (Societe Anonyme), Pulnoy (FR)

(*) Notice: Under 35 U.S.C. 154(b), the term of this patent shall be extended for 0 days.

(21) Appl. No.: 09/355,779

(22) PCT Filed: Jan. 22, 1998

(86) PCT No.: PCT/FR98/00112

§ 371 Date: Sep. 2, 1999

§ 102(e) Date: Sep. 2, 1999

(87) PCT Pub. No.: WO98/33475

PCT Pub. Date: Aug. 6, 1998

(30) Foreign Application Priority Data

Feb. 3, 1997 (FR) .................................................. 97/01325

(51) Int. Cl.⁷ .......................... A61K 38/00; A61K 31/35; A61K 47/00
(52) U.S. Cl. ............................. 514/2; 514/457; 514/460; 514/773
(58) Field of Search ................................ 514/457, 2, 773, 514/460

(56) References Cited

FOREIGN PATENT DOCUMENTS

| 11315007 | * | 11/1999 | (JP) . |
| WO 86/02833 | | 5/1986 | (WO) . |
| WO 94/18944 | | 9/1994 | (WO) . |
| WO 96/11667 | | 4/1996 | (WO) . |
| WO 96/28008 | | 9/1996 | (WO) . |

* cited by examiner

Primary Examiner—Marianne M. Cintins
Assistant Examiner—Vickie Kim
(74) Attorney, Agent, or Firm—Young & Thompson (57) ABSTRACT

The invention concerns a synergetic complex designed in particular for being incorporated in a cosmetic and/or pharmaceutical preparation for topical use on the skin and/or superficial body growth this complex is characterized in that it contains at least an extract of *Pisum Sativum* seeds rich in peptides, an extract of a plant of the Meliaceae family, rich in tannin and/or coumarin derivatives and, if required, at least an amino acid in the form of complex salt(s).

7 Claims, 4 Drawing Sheets

ACTIVE SYNERGETIC COMPLEX AND COSMETIC AND/OR PHARMACEUTICAL PRODUCT CONTAINING THIS COMPLEX

The present invention relates to the fields of cosmetology and pharmacology, particularly preventive and reparative, and has for its object an anti-stress active synergetic complex, as well as a cosmetic and/or pharmaceutical product including this latter.

In the cells of an organism, in particular human, stress can be produced either by external aggressions: heat, zenobiotic attack (cadmium, sodium arsenite), solar irradiation, or by glucose deficiency, oxygen deficiency (anoxia) or by endogenous origin: cellular division, cellular differentiation.

All living organisms, from the most simple (archeobacteria) to the most highly evolved (mammals), have the capacity to respond to stress by synthesis of a set of proteins known as HSP (Heat Shock Proteins) belonging to different families as a function of their molecular weight.

The mentioned aggressions give rise to a denaturizing of the cellular proteins ("proteotoxins") and the stress proteins (HSP) take place in "renaturing" of these proteins or in their elimination. They thus permit the cells to resist stress.

During stress, the activity of the proteins of the HSP type is also changed to protect the genetic patrimony (ADN) as well as its mode of expression (nucleol, ribosome, messenger ARN).

In the skin, there is found in the normal physiologic condition the expression of most of the stress proteins with in particular a strong expression of the proteins of the family HSP70, but also HSP27.

HSP72 is preferentially localized in the base layer and HSC70 (HSP constituent) in the suprabasal layers.

In the course of different cutaneous stresses, the expression of HSP in the cells increases significantly and these proteins can be considered as true cellular markers of stress.

It has thus been shown that for keratinocytes in culture, a hot thermal shock (1 hour at 42° C. or 15 minutes at 47° C.) induces the expression of HSP72, HSP78, HSP90 and HSP 119 and that a thermal shock (1 hour at 45° C.) induces the expression of HSP72 and HSP27 in human skin in organolyptic culture.

Similarly, in in vivo human skin, there is induction of HSP72 after a hot shock in the epidermal and dermal cells and the cutaneous stress arising from UV-B irradiation induces the appearance of HSP72 in organolyptic cultures of human skin and HSP27 in the skin of mice, in vivo.

Similarly, it has also been verified that a UV-A treatment (5 J/cm$^2$ at to 80 J/cm$^2$) induces the expression of HSP72 in cellular cultures (cellular line of fibrosarcome HT1080).

Thus, it is particularly well established that in the course of physical aggression such as heat or UV irradiation, the proteins of the HSP type are strongly induced at the level of the cutaneous epidermis. They thus represent an excellent marker of the degree of stress of the skin under these conditions: ultraviolet irradiation accompanied or not by temperature rise.

These markers (HSP) can therefore be perfectly used to study active agents and/or cosmetic products and particularly products for solar protection (solar products or against premature aging of the skin).

There exist at present a certain number of methods to evaluate the protective effect on the skin against damage from sunlight, solar preparations, measurement of SPF ("Sun Protecting Factor"), counting SBCs ("Sunburn Cells" in the epidermis, measurement of the anti-free radical effect.

The evaluation of HSP, and particularly HSP27 and 72, is an original method to measure the photoprotective effect of cosmetic products, anti-sun protectors or anti-premature aging of the skin, photo-induced.

It is known moreover that glutathione, a tripeptide composed of three amino acids of which cystine confers on this tripeptide a thiol (—SH) function, exists in the reduced form (GSH) or oxidized form (GS—SG disulfide bridge) in the cell thanks to an enzymatic system for conversion permitting passing from one form to the other and that the glutathione is present in a large quantity in the skin.

In comparison relative to the dermis, it is present in a quantity twice as great in the epidermis, in the layer of the living cells and in the layer of dead cells or corneal layer.

It is well known that in the skin, glutathione plays the role of detoxifier of free radicals and peroxides, and also for protection of the membranes of the living cells and the structural proteins of the corneal layer (keratin).

This detoxification and protective power is exerted under different conditions and natures of stress such as oxidative stress, thermal stress or irradiation stress.

Thus, as indicated above, ultraviolet radiation UV-B and also UV-A gives rise to a depletion of the quantity of glutathione, in the cells undergoing in vitro culture or in vivo culture on mice and it is has been demonstrated that this depletion potentializes the formation of cells of the type of sunburn cells in the skin.

It is also known that UV-R radiation increases the presence of the disulfide bridges (S—S) shown by histochemistry in the epidermis, in particularly in the sunburn cells that appear after irradiation.

These difulside bridges are moreover as a step preceding aptosis or UV-induced programmed cellular death.

The content in the skin of thiol groups, of which glutathione, and of disulfide bridges, are hence good indicators of development toward aging and accelerated cellular death, and it appears that the enrichment of the epidermis in thiol groups, and particularly glutathione, constitutes a good anti-solar protection and anti-photo-accelerated aging protection.

So as to combat the effects of solar radiation, different cosmetic products called "sunscreens" and "anti-sun aging" have been developed and distributed, their development from the beginning until now can be divided in several steps of which each corresponds substantially to the addition of a supplementary active compound.

It has been first of all proposed to introduce into these known products UV-B filters (to avoid sunburn), then to introduce UV-A filters (to act on chronic photo-aging and carcinogenesis).

A third step has consisted in adding anti-oxidant and anti-free radical substances (to combat the formation of sunburn cells), followed by the incorporation of pre-melanogenic substances (acceleration of bronzing by the production of auto-melanin) and, finally, more recently, by the introduction of cytophotoimmunoprotectors (preservation of the cutaneous immunological capital constituted by the Langerhaus cells in the epidermis).

Independently of the above development, which has led to products having a number of ingredients that increase without real synergesis between them, the inventors of the present application have sought and developed a new way consisting in the reinforcement of the natural autodefense of the skin, which is to say by acting on a biomolecular scale on the protection and repair of a sun-damaged skin, by the synergetic and simultaneous actions, on the one hand, of stimulation of autobiosynthesis of reduced glutathione and, on the other hand, by inhibition of the appearance of stress proteins, which are molecular markers of epidermal aggressions.

This research has permitted arriving at a synergetic complex having in particular photoprotective activities from biomolecular deleterious effects and adapted particularly to be integrated into a cosmetic and/or pharmaceutical preparation for topical use for the skin and/or the hair, nails and eyelashes, comprising at least one extract of seeds of *Pisum Sativum* rich in peptides, a plant extract of the family of meliaceae, rich in tannins and/or cumarin derivatives (and, as the case may be, in triterpenoids and/or in saponosids), and, at the case may be, at least one amino acid in the form of complex salt or salts.

This active synergetic complex is present preferably in concentrated form and easily usable by cosmetic formulators.

According to a first characteristic of the invention, the synergetic complex comprises between 0.05% and 40% by weight, preferably between 1% and 40% by weight, of an extract of *Pisum Sativum* rich in peptides, in the dehydrated form or not.

The process for preparation of the peptidic extract of seeds of *Pisum Sativum* can, by way of example, consist in crushing these seeds in the presence of acidulated water and carrying out agitation at 50° C., then centrifuging and performing an ultrafiltration of the obtained suspension, and finally filtering the retantate and if desired dehydrating it by atomization or lyophilization.

According to another characteristic of the invention, the synergetic compound comprises between 0.005% and 10% by weight, preferably between 0.1% and 10% by weight, of an extract of a plant of the meliaceae family rich in tannins and/or cumarin derivatives.

Preferably, the extract of the plant of the family meliaceae consists in an aqueous, alcoholic or hydroalcoholic dehydrated aqueous extract of *Khaya Senegalensis*, preferably an extract of the bark of this plant or, as the case may be, an extract of the leaves or the seeds of this latter.

The process for production of the bark of *Khaya Senegalensis* can consist for example in crushing the bark of this plant, then emplacing it in 20% suspension in distilled water, agitating for two hours at 90° C. or leaving a maceration at ambient temperature for two days, and finally effecting a separation and a filtration, followed if desired by a dehydration (atomization or lyophilization).

The extraction of the active fraction (comprising particularly tannins and/or cumarin derivatives) can also be carried out under the same conditions by using as the solvent ethanol or a water/ethanol mixture.

According to another characteristic of the invention, the amino acid or the amino acids present belong to the group formed by histidine, arginine and tyrosine, said amino acid or acids being present in the form of succinic acid salts and/or aspartic acid.

Preferably, the amino acids are present in pure form, in the form of succinic and/or aspartic acid salts or in the form of mixtures of these (amino acid salt or amino acid/succinic acid or aspartic acid), representing together between 0.05% and 40% by weight, preferably between 0.1% and 40% by weight, of the active synergetic complex.

In addition to the mentioned components, the synergetic complex according to the invention can also comprise (i) between 0.05% and 5% by weight of a hydrosoluble extract of yeast cells, of the *Saccharomyces Cerevisiae* type, (ii) between 0.05% and 10% by weight of monosaccharides, of saccharides, polyosides and/or polysaccharides, particularly saccharose and/or glycogen, and/or (iii) between 0.01% and 10% by weight of B group vitamins, such as particularly pyridoxin and/or niacinamide.

Given the characteristic differences mentioned above, a weight formulation of the type of an active synergetic complex according to the invention can be present as follows:

| | |
|---|---|
| 1) peptidic extract of seeds of Pisum (peas) | 1 to 40% |
| 2) aqueous or hydroalcoholic extract of the bark of Khaya Senegalensis | 0.1 to 10% |
| 3) amino acids (histidine, arginine and/or tyrosine) in the form of succinic and/or aspartic acid salt or salts | 0.1 to 40% |
| 4) hydrosoluble extract of yeast | 0.05 to 5% |
| 5) vitamin B (pyridoxine and/or niacinamide) | 0.01 to 10% |
| 6) polosid (glycogen) | 0.05 to 10% |
| 7) excipient and/or solvent | qsp 100% |

The mentioned synergetic complex can be prepared in various galenic forms such as liquid, solution, paste, powder, liposomes, microspheres, microcapsules, nanoparticles or the like.

Examples 1 to 7 hereafter show in a non-limiting way different possible weight formulations (expressed in %) for the active synergetic complex according to the invention.

Example 1:

| | | |
|---|---|---|
| Powdered peptidic extract of Pisum Sativum | | 30.00 |
| Lyophilized aqueous extract of Khaya Senegalensis bark | | 2.00 |
| Sorbitol | qsp | 100.00 |

Example 2:

| | | |
|---|---|---|
| Peptidic extract of Pisum Sativum | | 30.00 |
| Lyophilized aqueous extract of K. Senegalensis bark | | 2.00 |
| Histidine salt of succinic acid | | 2.00 |
| Arginine salt of succinic acid | | 3.00 |
| Arginine aspartate | | 2.00 |
| Tyrosine | | 1.00 |
| Hydrosoluble extract of Saccharomyces Cerevisiae | | 2.00 |
| Sorbitol | qsp | 100.00 |

Example 3:

| | | |
|---|---|---|
| Peptidic extract of Pisum Sativum | | 30.00 |
| Lyophilized aqueous extract of K. Senegalensis bark | | 0.50 |
| Histidine salt of succinic acid | | 1.00 |
| Arginine salt of succinic acid | | 5.00 |
| Arginine aspartate | | 0.50 |
| Tyrosine | | 1.00 |
| Hydrosoluble extract of Saccharomyces Cerevisiae | | 2.00 |
| Mannitol | qsp | 100.00 |

Example 4:

| | | |
|---|---|---|
| Peptidic extract of Pisum Sativum | | 15.00 |
| Extract of the bark of K. Senegalensis | | 5.00 |
| Histidine and arginine succinate | | 10.00 |
| Tyrosine | | 1.00 |
| Glycogen | | 5.00 |
| Sorbitol | qsp | 100.00 |

Example 5:

| | | |
|---|---|---|
| Powdered peptidic extract of Pisum Sativum | | 10.00 |
| Extract of bark of K. Senegalensis (lyophilisate) | | 5.00 |
| Histidine and arginine succinic acid salt | | 20.00 |
| Arginine aspartate | | 2.00 |
| Tyrosine | | 1.00 |
| Pyridoscine. HCl | | 3.00 |
| Sorbitol | qsp | 100.00 |

-continued

Example 6:

| | | |
|---|---|---|
| Peptidic extract of Pisum Sativum | | 20.00 |
| Hydroalcoholic extract of bark of K. Senegalensis (lyophilisate) | | 0.50 |
| Histidine and arginine succinic acid salt | | 10.00 |
| Arginine aspartate | | 5.00 |
| Tyrosine | | 1.50 |
| Hydrosoluble extract of Saccharomyces Cerevisiae | | 3.00 |
| Mannitol | qsp | 100.00 |

Example 7:

| | | |
|---|---|---|
| Peptidic extract of Pisum Sativum (atomisate) | | 10.00 |
| Aqueous extract of bark of K. Senegalensis (lyophilisate) | | 1.00 |
| Succinic acid/histidine (25/75) | | 4.50 |
| Arginine/aspartic acid (75/25) | | 4.75 |
| Tyrosine | | 1.00 |
| Hydrosoluble extract of Saccharomyces Cerevisiae (lyophilisate) | | 1.50 |
| Pyridoxine. HCl | | 1.00 |
| Mannitol | qsp | 100.00 |

The present invention also has for its object the use of a synergetic complex as described above as an active compound for the preparation of a composition or of a cosmetic and/or pharmaceutical product for topical usage for the skin and/or hair, nails and eyelashes.

Said synergetic compound can be used as a cutaneous anti-stress active agent, shown by the reduction of the expression of the stress proteins known as HSP, particularly HSP27, induced in the epidermis upon stress of the UV-A, UV-B and visible solar irradiation type, and/or to heating of the skin.

It thus prevents or inhibits the appearance of stress proteins induced by solar irradiation and reduces as a result the undesirable effects of the local inflammation type and free radicals generated by these irradiations.

Said synergetic complex can also be used, on the one hand, as an agent for stimulating the autosynthesis of reduced glutathione, by the cutaneous or capillary cells and/or, on the other hand, as an agent against the appearance of disulfide bridges induced by acute solar irradiation or resulting from photo-induced chronic cutaneous aging.

Preferably, it is integrated into a product of the solar or after-sun protective type, only or in complementary association with solar filters, or in a product for day care of the skin, with preventive and/or reparative action against the effects of aging and/or anti-pollution (in association or not with solar filters).

Finally, the present invention also has for its object a cosmetic and/or pharmaceutical product for the skin and/or the hair, nails or eyelashes (liquid, lotion, emulsion, cream or the like), having particularly a molecular cytophotoprotective activity, characterized in that it comprises between 0.01% and 90% by weight, preferably between 0.05 and 20% by weight, of an active synergetic complex as described above, if desired associated with solar filters.

The cosmetic and/or pharmaceutical product described comprises, in a preferred manner, between 1 and 10% by weight of the active synergetic complex according to the invention and there is observed, following external topical applications of said product, a protective, photoprotective and local anti-inflammatory effect.

By way of non-limiting examples of practical embodiments of compositions according to the invention, there will be hereafter described different cosmetic products or preparations comprising the active synergetic complex described:

EXAMPLE 1

A cosmetic product in the form of anti-stress emulsion for the face according to the invention could for example have a weight composition, constituted from fractions A, B and C as follows, as indicated hereafter.

Fraction A:

| | |
|---|---|
| Glycerol stearate (and) PEG 100 stearate | 1.500 |
| Glycerol stearate (and) CETETH-20 | 1.500 |
| Cetyl alcohol | 1.000 |
| Caprylic/capric triglyceride | 5.000 |
| Cetostearylic isononanoate | 4.000 |
| Octyldodecanol | 3.000 |
| Dimethicone | 0.500 |
| Elestab 4121 (Laboratoires Serobiologiques) | 0.300 |

Fraction B:

| | |
|---|---|
| Water | 73.550 |
| Elestab 4112 (Laboratoires Serobiologiques) | 0.400 |
| Glycerine | 5.000 |
| Xanthin gum | 0.500 |
| Active synergetic complex (example 6) | 5.000 |

Fraction C:

| | |
|---|---|
| Polyacrylamide and isoparaffine (and) Laureth-7 | 0.750 |

The process of preparation and production of the emulsion for the face mentioned above consists essentially in preparing Fraction B (dissolution of Elestab 4112 in water and addition of glycerin at 75° C., then addition of the xanthin gum and dissolution of the synergetic complex), preparing Fraction A at 75° C. and pouring it into Fraction B at 75° C., with turbine agitation, then adding Fraction C at 60° C., with turbine agitation, cooling and using planetary action starting at 50° C. until it returns to ambient temperature.

EXAMPLE 2

A cosmetic product in the form of a protective and anti-aging cream for the neck, according to the invention could, for example, have a weight composition, constituted from the following fractions A and B, as indicated hereafter.

Fraction A:

| | |
|---|---|
| Sorbitol palmitate | 3.500 |
| Glycerol stearate | 1.500 |
| Cetyl alcohol | 2.500 |
| Cetostearylic isononanoate | 7.000 |
| Octyldodecanol | 2.500 |
| Paraffin oil | 3.000 |
| Dimethicone | 2.000 |
| Elestab 4121 (Laboratoires Serobiologiques) | 0.300 |

Fraction B:

| | |
|---|---|
| Water | 69.100 |
| Elestab 4112 (Laboratoires Serobiologiques) | 0.400 |
| Glycerin | 4.000 |
| Sodium cetostearylic sulfate | 1.200 |
| Active synergetic complex (example 3) | 2.000 |

The process for preparation and production of the mentioned cream consists essentially in preparing fraction B at 7500° C., pouring into it with turbine agitation fraction A at 80° C., letting it cool and maintaining turbine agitation, down to 50° C., then continuing cooling with planetary agitation, until it returns to ambient temperature.

EXAMPLE 3

A cosmetic product in the form of a solar cream according to the invention could for example have a weight composition, constituted from the following fractions A and B, as indicated hereafter.

| Fraction A: | |
|---|---|
| Cetyl alcohol | 5.000 |
| Caprylic/capric triglyceride | 6.100 |
| Paraffin oil | 3.750 |
| Lanolin | 1.000 |
| Glycerol stearate | 2.000 |
| Dimethicone | 0.250 |
| Octyldodecanol | 4.500 |
| Octyl stearate | 8.150 |
| Octyl methoxycinnamate | 6.800 |
| Butyl methoxybenzoyl methane | 2.000 |
| Elestab 4121 (Laboratoires Serobiologiques) | 0.300 |
| Fraction B: | |
| Water | 53.750 |
| Glycerin | 3.000 |
| Potassium cetylic phosphate | 3.000 |

The process of preparation and production of the mentioned solar cream consists essentially in preparing fraction A and fraction B at 75° C., then pouring fraction A, with turbine agitation, into fraction B at 75° C. and cooling the mixture to ambient temperature with planetary agitation.

EXAMPLE 4

A cosmetic product in the form of solar cream according to the invention could for example have a weight composition, constituted from the following fractions A and B, as indicated hereafter.

| Fraction A: | |
|---|---|
| Cetyl alcohol | 5.000 |
| Caprylic/capric triglyceride | 6.100 |
| Paraffin oil | 3.750 |
| Lanolin | 1.000 |
| Glycerol stearate | 2.000 |
| Dimethicone | 0.250 |
| Octyledodecanol | 4.500 |
| Octyl Stearate | 8.150 |
| Octyl Methoxycinnamate | 6.800 |
| Butyl Methoxybenzyl Methane | 2.000 |
| Elestab 4121 (Laboratoires Serobiologiques) | 0.300 |
| Fraction B: | |
| Water | 50.750 |
| Elestab 4112 (Laboratoires Serobiologiques) | 0.400 |
| Glycerin | 3.000 |
| Potassium cetyl phosphate | 3.000 |
| Synergetic complex (example 7) | 3.000 |

The process of preparation and production of the mentioned solar cream consists essentially in preparing fraction A at 80° C. and fraction B at 75° C., then pouring fraction A at 85° C. with turbine agitation into fraction B at 75° C. and cooling the mixture to ambient temperature with planetary agitation.

So as to illustrate and demonstrate the advantages of the complex agents according to the mentioned examples (their original properties and their interest and specificity relative to solar filters for UV-B and UV-A), objectivation tests according to A, B, C, D and E have been carried out with the active synergetic complex corresponding to example 7 described above.

The results of these tests have been set forth in graphic manner in FIGS. 1 to 8 of the accompanying drawings, in which.

A) Nutritive and eutropic activity on surviving human fibroblasts (in vitro).

The eutropic capacities of the active synergetic complexes according to the invention have been evaluated by a survival test on human fibroblasts MRC5. The doses to be tested have been first determined by a test of toxicity on fibroblasts MRC5.

For the survival test, the product has been dissolved in a standard culture medium DMEM and contacted with the MRC5 three days after seeding. Then at the end of seven hours of incubation at 37° C. ($CO_2$=5%), the survival of the cells has been evaluated by dosage of intracellular glutathione (GHS) with a fluorescent marker (OPTH), according to the method of P. J. HISSIN and R. HILF.

Figure 1:
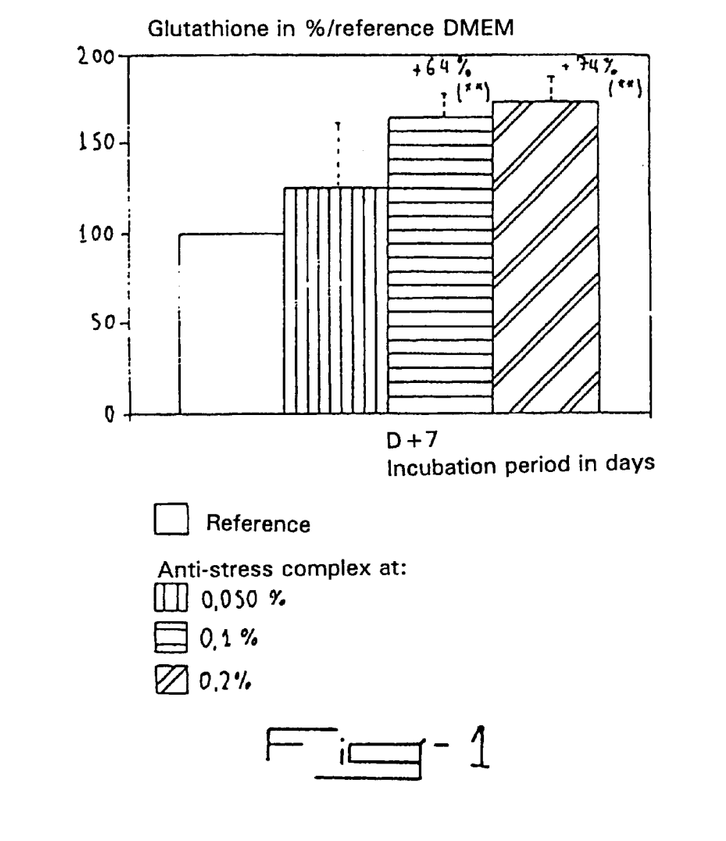
FIG. 1 is a graphic representation of the amount of glutathione of the human fibroblasts MRC5 in a survival test (test of activity A) [Test of student-(**) indicates that p<0.01]

The anti-stress complex significantly improved the content of GSH of surviving MRC5: +64% and +74% per J+7 for 0.1 and 0.2% (see FIG. 1).

B) Anti-free radical activity (tests in tubo)

The anti-free radical capacities have been evaluated by a battery of tests covering the initial radical forms as well as the reactive forms of induced oxygen.

1) Anti-free radical test on DPPH°: this test evaluated the capacities of the synergetic complex to stabilize a colored free radical, diphenylpycrylhydrazyl (DPPH°) in its stable leucoderivative.

2) Anti-hydroxyl radical tests (OH°) by the Fenton reaction: these tests evaluated the capacities to scavenge OH° formed by iron with $H_2O_2$ and disclosed by salicylic acid (colored reaction) or by desoxyribose (desoxyribose is an essential compound of ADN, and its oxidation products by OH° are disclosed by thiobarbiturate acid). Moreover, a test is carried out without EDTA to determine the capacities to detect iron (ferriprive effect).

3) Anti-superoxide anion tests ($O_2^{-*}$): $O_2^{-*}$ is produced during oxidative stress by induction of xanthine oxidase which degrades the coenzymes NAD(P) and hypoxanthine in excess by stopping the energetic metabolism of the tissues ($O_2^{-*}$ dismutes spontaneously or in the presence of superoxide dismutase in $H_2O_2$).

These biochemical tests were carried out by mixing hypoxanthine and xanthine oxidase and developing $O_2^{-*}$ with luminol or developing $O_2^{-*}$ and $H_2O_2$ with luminol+ microperoxidase.

The results (the table below) show that the active synergetic complex according to the invention has a wide spectrum of anti-free radical activity, covering not only the initial radical forms (DPPH°) but also the reactive forms of induced oxygen (OH°, $O_2^{-*}$ and $H_2O_2$) as well as a ferriprive activity demonstrated by the Fenton reaction on desoxyribose without EDTA (CI50=0.23%). (C150=product concentration which reduces by 50% the intensity of the enzymatic reaction–p/v=weight/volume)

| Tests | C150 (in % p/v) |
| --- | --- |
| Chemical tests: | |
| DPPH° | C150 = 0.36% |
| Fenton reaction: Salicylic acid | C150 = 0.12% |
| Desoxyribose | |
| with EDTA | C150 = 0.14% |
| without EDTA | C150 = 0.23% |
| Biochemical tests: | |
| Method with luminol | C150 – 0.04% |
| Method with luminol + microperoxydase | C150 = 0.70% |

C) Anti-inflammatory cytophotoprotective activity as to UV-B (in vitro test)

UV-B triggers an inflammatory process (erythema, edema) by activation of an enzyme, phospholipase A2, which releases arachidonic acid (unsaturated fatty acid) from biological membranes.

Arachidonic acid is the precursor of the inflammation mediators such as the prostaglandins and the leucotrienes.

Prostaglandins (of which PGE2 is one) are formed by the action of cyclo-oxygenase, then are secreted from the cell and act by means of specific receptors (edema, erythema, immunosuppression).

The leucotryenes are formed by the lipogenases and act (as do the prostaglandins) on specific receptors. Thus, leucotryene LTB4 attracts and activates the polynuclear neutrophiles which liberate free radicals and proteases destroying tissues.

The activity of lipogenase also produces superoxide anions which amplify the oxidative stress induced by the prostaglandines and the leucotrienes.

The anti-PGE2 effect of the active synergetic complex according to the invention has been studied in a culture of human keratinocytes, brought to saturation in vitro.

The growth medium is replaced by a glucose saline solution (containing various concentrations of this synergetic complex) then the cultures are irradiated (30 mJ/cm²; fluorescent tube UV-B) and incubated again overnight at 37° C., $CO_2$=5%.

The number of cells has been quantified after trypsination by a particle counter. In the supernatant medium, the quantity of PGE2 has been evaluated by an ELISA test whilst the quantity of LDH (lactate dehydrogenase) has been measured by an enzymatic reaction (DO at 340 nm).

The inhibition of lipoxygenase has been determined in tubo by quantification of the superoxide anions (by luminescence) produced by this enzyme in the presence of unsaturated fatty acids.

Figure 2:
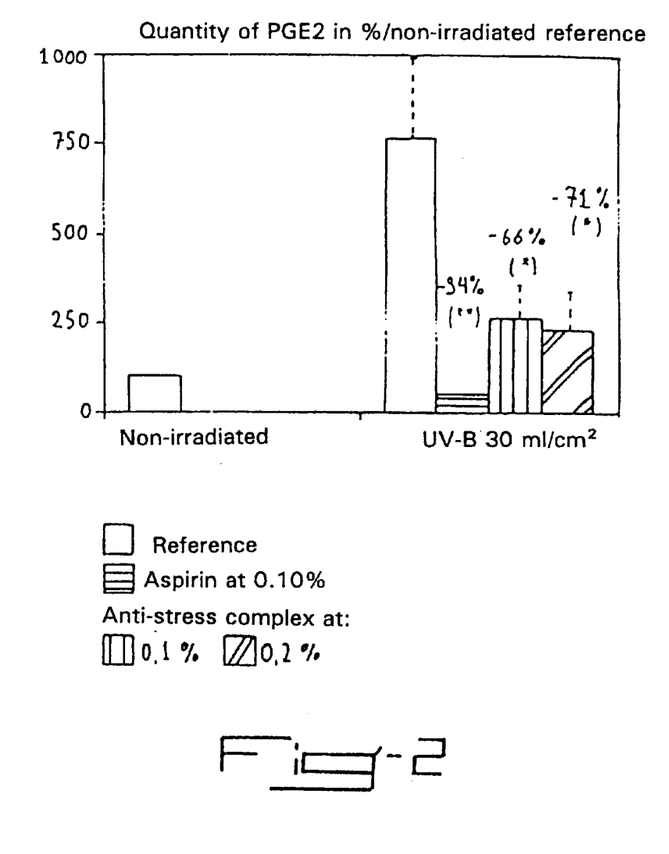
FIG. 2 is a graphic representation of the quantity of PGE2 (prostaglandin E2) of human keratinocytes NCTC2544 under UV-B radiation (30 mJ/cm$^2$)–test of activity C [Test t of student-(*) indicates that p<0.05 and (**) indicates that p<0.01]
Figure 3:
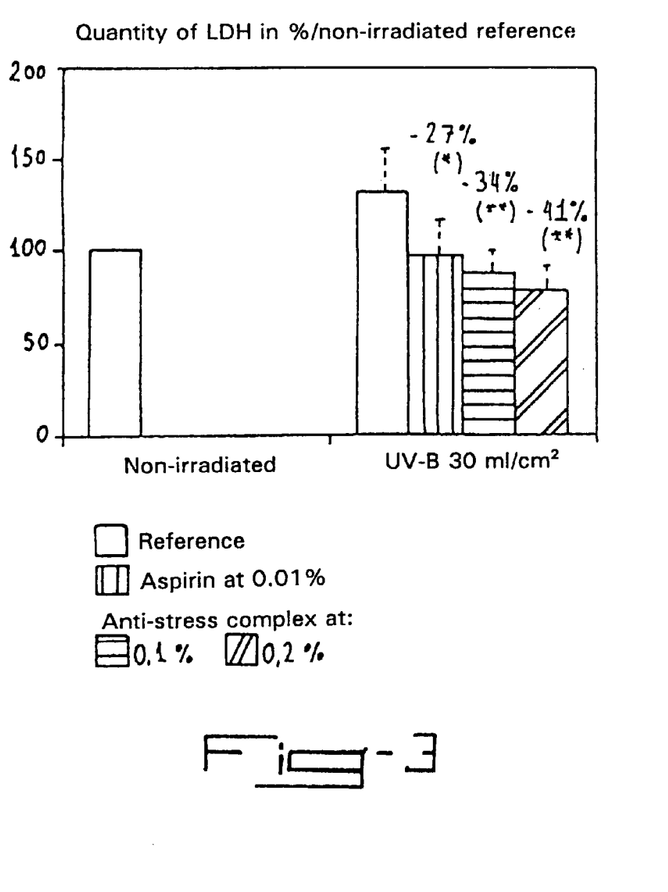
FIG. 3 is a graphic representation of the quantity of LDH (lactate dehydrogenase salted out from the supernatant culture medium) of human keratinocytes NCTC2544 under UV-B radiation (30 mJ/cm$^2$)–test of activity C/simultaneous treatment [test t of student-(*) indicates that p<0.05 and (**) indicates that p<0.001]'
Figure 4:
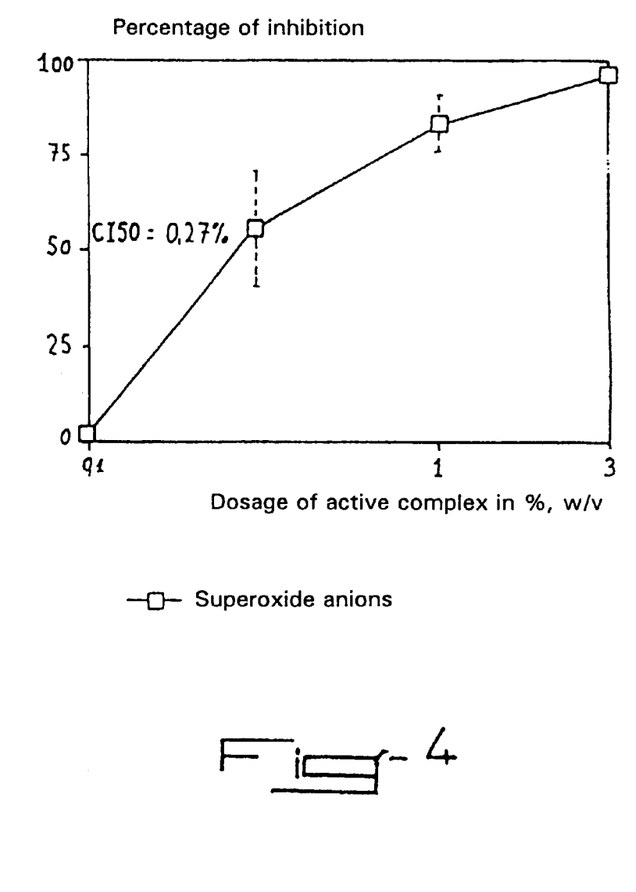
FIG. 4 is a graphic illustration of the percentage of inhibition of lipoxygenase by dosage of the superoxide anions formed in tubo–test of activity C.

The synergetic complex according to the invention (0.2%, p/v) (see FIGS. 2, 3 and 4) has greatly reduced the quantity of PGE2 (−71%) and of LDH (−41%) salted out after UV-B irradiation.

The synergetic complex has a C150 of 0.27% (p/v) relative to superoxide anions induced by lipoxygenase.

Compared to aspirin, the anti-stress complex is less active as to PGE2 but, on the contrary, is more active as to LDH (which characterizes the membrane suffering) and relative to lypoxygenase.

The synergetic complex according to the invention has anti-inflammatory capacity following UV-R radiation not only by inhibition of the cyclo-oxygenase and by cytophotoprotection of the biological membranes, but also by capture of the superoxide anions produced by the activity of the lipoxygenases on the unsaturated fatty acids.

D) Cytophotoprotective activities relative to UV-A and stimulating autosynthesis of glutathione (in vitro test on human fibroblasts MRC5)

Fibroblasts MRC5 have been cultured in a growth medium until saturation of the cellular mat.

Then, the growth medium was replaced by a standard medium containing the synergetic complex at various concentrations to be tested.

After incubation for 48 hours at 37° C., the different media were replaced by a saline solution, then the MRC5 was irradiated (by UV-A tubes).

At the end of irradiation, the saline solution was recovered, for determination of the malonaldialdehyde (MDA) by reaction with hot thiobarbituric acid (fluorescence at 560 nm). The MRC5 cells were recovered for the determination of proteins (Bradford method) and of glutathione (GSH) by a fluorescent probe (MDA is a degradation product of unsaturated lipids which comprise the biological membranes and it causes bridges which inhibit the enzymes and form lipofuscines (aging pockets) and would be mutagenic).

Figure 5:
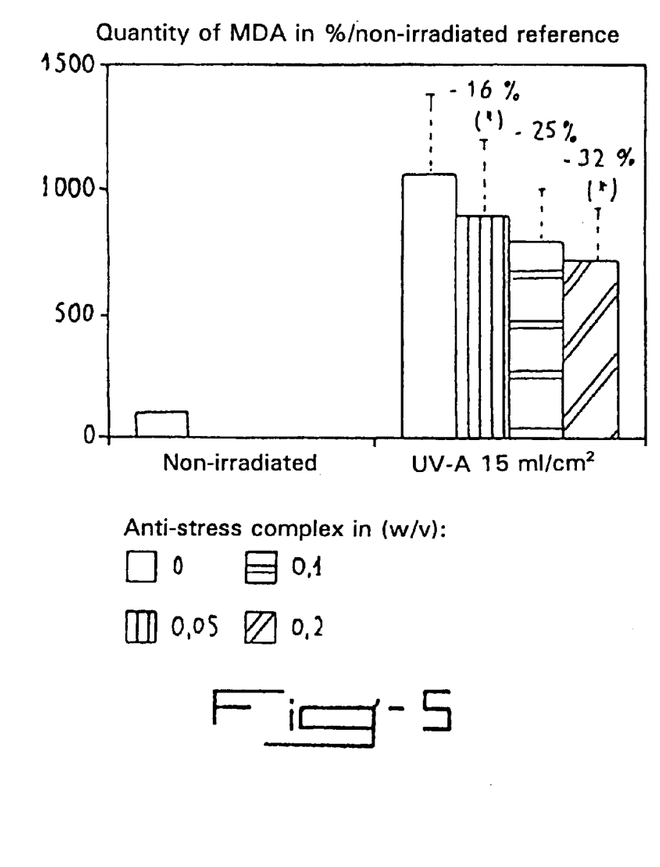
FIG. 5 is a graphic illustration of the quantity of MDA (malonaldialdehyde) of fibroblasts MRC5 under UV-A radiation (15 J/cm$^2$)—test of activity D/preventive treatment [(*) indicates that p<0.05]
Figure 6:
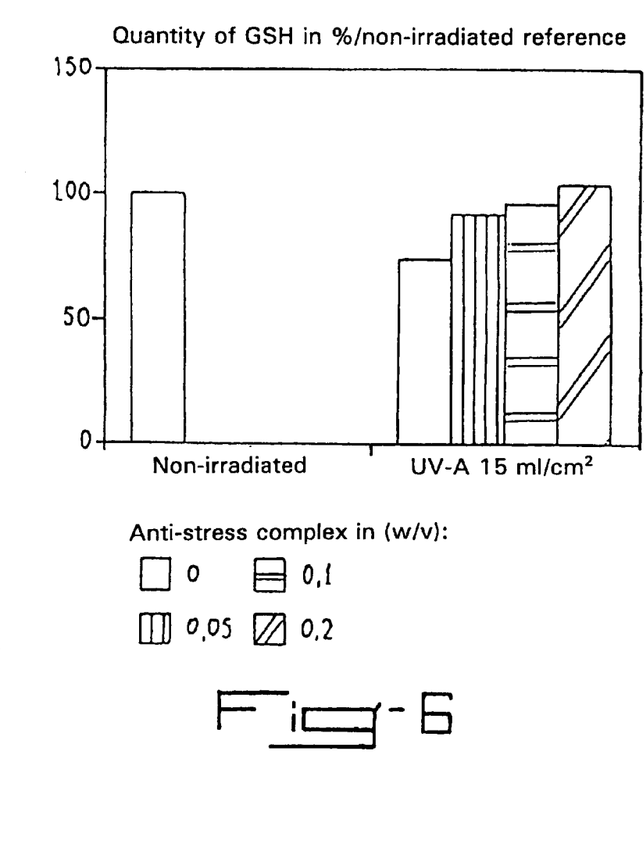
FIG. 6 is a graphic illustration of the quantity of GSH (reduced glutathione) of fibroblasts MRC5 under UV-A radiation (15 J/cm$^2$)–test of activity D/preventive treatment [Test t of student-(*) indicates that p<0.05]

The results (see FIGS. 5 and 6) show that UV-A (15 J/cm²) strongly induced the secretion of MDA (x 10) and caused to fall by about 25% the quantity of GSH in the MRC5.

The active synergetic complex according to the invention reduced the lipoperoxydation induced by the UV-A: −32% for the quantity 0.2% (p/v).

The synergetic complex inhibited the destruction of GSH by UV-A: +41% for a quantity of 0.2% (p/v).

The synergetic complex has therefore reduced the lipoperoxydation of the fiberblasts, induced by UV-A, particularly by increase of the quantity of reduced glutathione.

E) Anti-stress protein activity and anti-disulfide bridges (test on human skin ex vivo)

The object of this last study was to test the anti-solar effectiveness of the active synergetic complex at 3% in association with a mixture of UV-A+UV-B filters, compared to these solar filters alone, during cutaneous irradiation, ex vivo, by a solar simulator.

So as to evaluate the anti-solar effectiveness of the anti-stress complex, the irradiation of human skin in organotypical culture (ex vivo), has been carried out with or without topical treatment by the solar products to be tested, whose composition has been set forth in examples 3 and 4 above.

The activity of the products was then evaluated by immunohistochemistry+analysis of the images on two solar stress markers: the induction of the stress protein HSP27 and the appearance of disulfide bridges (S—S) in the living layers of the epidermis.

Figure 7:
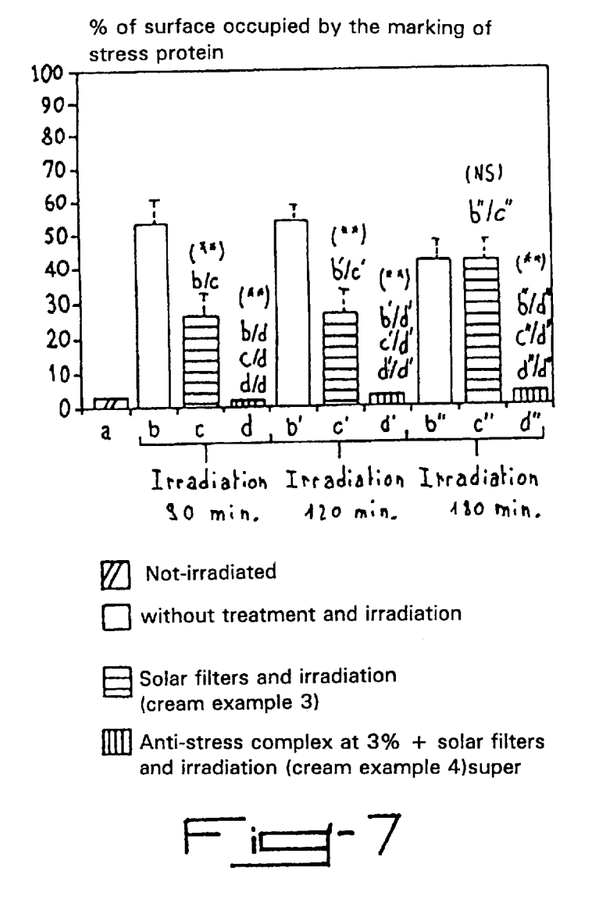
FIG. 7 is a graphic illustration showing the protective effect on human skin, ex-vivo, in organotypic culture, before irradiation with a solar simulator, in comparison to the induction of the stress protein HSP27 visualized by immunohistochemistry, in the living layers of the epidermis–test activity E [U of Mann et Whitney-() indicates that p<0.001 and (NS) is said to be "insignificant"]; and, FIG. 8 is a graphic illustration showing the protective effect on human skin, ex-vivo, in organotypic culture, before irradiation with a solar simulator, in comparison to the induction of S—S bridges of visualized histochemistry, in the living layers of the epidermis–test of activity E [U of Mann and Whitney-() indicates that p<0.001 and (NS) can be called "insignificant"].
Figure 8:
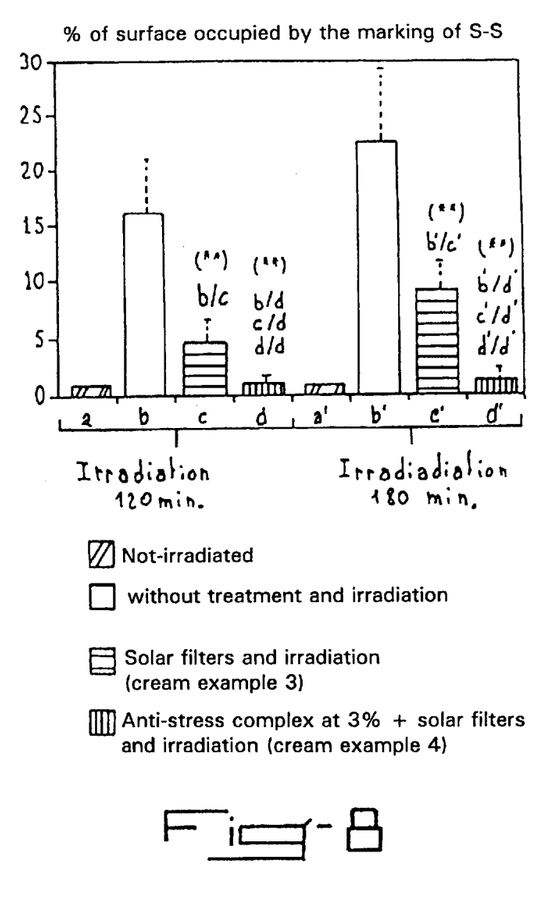

The results of experimentation (see FIGS. 7 and 8) have permitted concluding that:

in the epidermis of the unstressed normal human skin, the stress protein HSP27 is not expressed and the disulfide bridges are not present except at the level of the corneum stratum, for the three irradiation times studied, there is observed a very great induction of the stress protein, numerous disulfide bridges appear in the living layers of the epidermis for the two highest irradiation times, the use of creams containing solar filters, before irradiation, in most cases partially limits the induction of the stress protein and, in all cases, the appearance of S—S bridges, on the contrary, the application of the cream containing the active synergetic complex, before irradiation, almost completely avoids the expression of the stress protein HSP27 and the appearance of S—S bridges in the living layers of the human epidermis.

Of course, the invention is not limited to the embodiment described and shown in the accompanying drawings. Modifications remain possible, particularly as to the constitution of the various elements or by substitution of technical equivalents, without thereby departing from the scope of protection of the invention.

What is claimed is:

1. A photoprotective composition for topical application, comprising at least one extract of seeds of *Pisum Sativum* rich in peptides, and a plant extract from the family melicea rich in at least one of tannins and cumarin derivatives, in admixture in a dermatologically acceptable excipient.

2. A photoprotective composition as claimed in claim 1, including at least one amino acid in the form of at least one complex salt.

3. A photoprotective composition as claimed in claim 1, wherein said *Pisum Sativum* extract is present in an amount by 0.05 to 40% by weight of the whole.

4. A photoprotective composition as claimed in claim 1, wherein said plant extract of the family melicea is present in an amount between 0.005 and 10% by weight of the whole.

5. A photoprotective composition as claimed in claim 1, wherein said plant extract from the family melicea comprises an extract of *Khaya Senegalensis*.

6. A photoprotective composition as claimed in claim 1, wherein said at least one amino acid is at least one member selected from the group comprised by histidine, arginine and tyrosine.

7. A photoprotective composition as claimed in claim 6, wherein said amino acids are present in the form of said at least one of succinic acid salts and aspartic acid salts.

* * * * *